United States Patent
Blauch et al.

[11] Patent Number: 5,263,360
[45] Date of Patent: Nov. 23, 1993

[54] LOW PERMEABILITY SUBTERRANEAN FORMATION TESTING METHODS AND APPARATUS

[75] Inventors: Matthew E. Blauch, Duncan; David E. McMechan, Marlow; James J. Venditto, Duncan; Gregory L. Tanaka, Marlow, all of Okla.

[73] Assignee: Halliburton Company, Duncan, Okla.

[21] Appl. No.: 903,695

[22] Filed: Jun. 24, 1992

Related U.S. Application Data

[63] Continuation-in-part of Ser. No. 870,546, Apr. 17, 1992.

[51] Int. Cl.$^5$ .................... G01N 15/08; E21B 49/02
[52] U.S. Cl. ........................... 73/38; 73/153; 166/250
[58] Field of Search ............. 166/250; 73/38, 153, 73/155

[56] References Cited

U.S. PATENT DOCUMENTS

| | | | |
|---|---|---|---|
| 2,821,680 | 1/1958 | Slusser et al. | 73/38 |
| 3,181,346 | 5/1965 | Davies | 73/38 |
| 3,420,093 | 1/1969 | Collins | 73/38 |
| 3,839,899 | 10/1974 | McMillen | 73/38 |
| 4,233,840 | 11/1980 | Goss et al. | 73/153 |
| 4,253,327 | 3/1981 | Wiley | 73/38 |
| 4,458,520 | 7/1984 | Adame et al. | 73/38 |
| 4,487,056 | 12/1984 | Wiley | 73/38 |
| 4,555,934 | 12/1985 | Freeman et al. | 73/38 |
| 4,573,342 | 3/1986 | Jones | 73/38 |
| 4,599,891 | 7/1986 | Brauer et al. | 73/38 |
| 4,627,270 | 12/1986 | Jones | 73/38 |
| 4,753,107 | 6/1988 | Reed et al. | 73/38 |
| 4,842,073 | 6/1989 | Himes et al. | 166/294 |
| 4,922,758 | 5/1990 | Penny | 73/38 |
| 5,079,948 | 1/1992 | Collins et al. | 73/153 |

FOREIGN PATENT DOCUMENTS

| | | |
|---|---|---|
| 262348 | 12/1985 | Fed. Rep. of Germany . |
| 649989 | 2/1979 | U.S.S.R. ............. 73/38 |

*Primary Examiner*—Hezron E. Williams
*Assistant Examiner*—George Dombroske
*Attorney, Agent, or Firm*—Robert A. Kent; C. Clark Dougherty, Jr.

[57] ABSTRACT

The present invention provides methods and apparatus for determining the gas permeability of very low permeability subterranean formations as well as the gas permeability reducing effects of injecting one or more treatment fluids thereinto. A gas is injected into a core sample of the formation at a selected substantially constant pressure, and the injection is continued for a long period of time to insure steady state flow conditions. The temperature of the gas as it flows through the core sample and the flow rate of the gas exiting the core sample are measured, and the native state gas permeability of the core sample is calculated therefrom. One or more treatment fluids can be injected into the core sample after the native state permeability is determined. Thereafter, the gas permeability can again be determined and compared to the native state permeability.

10 Claims, 2 Drawing Sheets

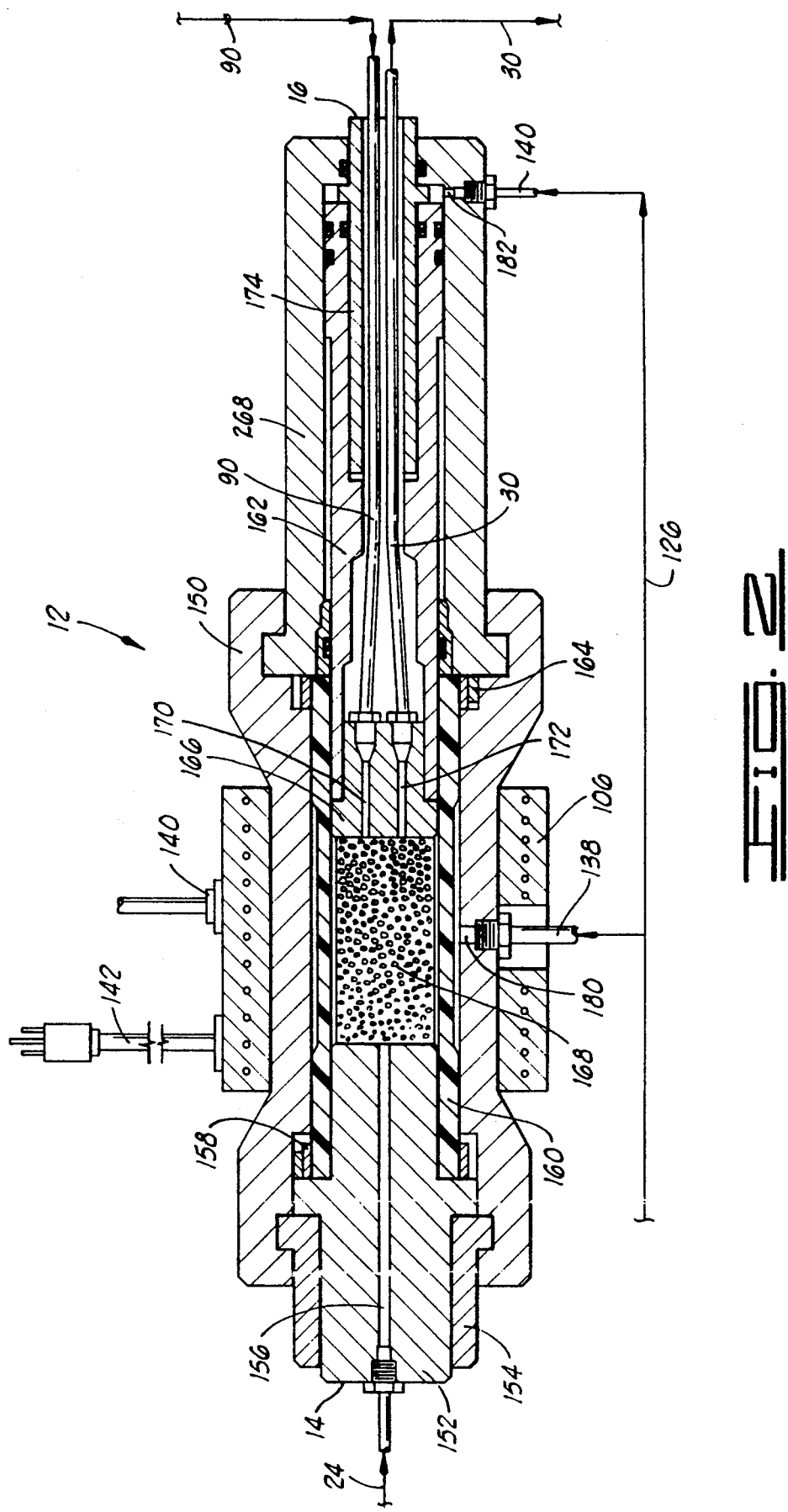

LOW PERMEABILITY SUBTERRANEAN FORMATION TESTING METHODS AND APPARATUS

This application is a continuation-in-part of application Ser. No. 07/870,546 filed Apr. 17, 1992.

BACKGROUND OF THE INVENTION

1. Field of the Invention

This invention relates to low permeability subterranean formation testing methods and apparatus, and more particularly, to methods and apparatus for testing core samples of low permeability formations to determine the gas permeabilities thereof and the gas permeability reducing effects of injecting one or more treatment fluids therein.

2. Description of the Prior Art

Various methods and apparatus have heretofore been developed for testing core samples of subterranean formations to determine various properties thereof including the permeabilities of the formations and the permeability reducing effects of injecting treatment fluids into the formations. Such methods and apparatus have included the use of a core sample test container known as a "Hassler sleeve" in which a core sample is confined and pressure is applied to the periphery thereof to simulate the confining stress of the formation from which the core sample was taken. The permeability of the core sample is determined, a treatment fluid is injected into the core sample and after the removal of treatment fluid, the permeability of the core sample is again determined. A comparison of the core sample permeabilities before and after the injection of the treatment fluid is then made to determine the reduction, if any, in the permeability of the core sample caused by the treatment fluid.

U.S. Pat. No. 4,842,073 issued on Jun. 27, 1989 to Himes et al. discloses such a core sample testing method and apparatus. As shown in the drawing, the apparatus of Himes et al. includes a Hassler sleeve and means for injecting nitrogen through a core sample confined within the Hassler sleeve to simulate the production of gas from the formation. Means for injecting a treatment fluid through the core sample in the opposite direction are also provided to simulate the injection of a treatment fluid into the formation. The percent of permeability recovery of the core sample after injecting a treatment fluid therein is determined by comparing the nitrogen permeability of the core sample before and after the treatment fluid injection.

While the prior methods and core sample testing apparatus have been utilized successfully in testing core samples of subterranean formations having normal permeabilities, such methods and apparatus have been unsuccessful in testing subterranean formation core samples of extremely low gas permeabilities, e.g., gas permeabilities in the range of from about $1 \times 10^3$ to about $1 \times 10^{-3}$ micro-darcies. Thus, there is a need for improved test methods and apparatus which can be utilized for determining the gas permeabilities of such subterranean formations as well as the effects of treatment fluids thereon.

SUMMARY OF THE INVENTION

The present invention provides improved methods and apparatus for determining the gas permeabilities of low permeability subterranean formations which meet the above described need and overcome the shortcomings of the prior art.

The methods of the present invention for determining the gas permeability of a subterranean formation wherein such permeability is in the range of from about $1 \times 10^3$ to about $1 \times 10^{-3}$ micro-darcies basically comprise confining a core sample of the formation within a test container and applying pressure on the periphery of the core sample to simulate the confining stress of the formation and to seal the sides of the core sample whereby fluid injected into one end of the core sample is forced to flow through the core sample to the other end. A gas is injected into the core sample by way of a first end thereof at a selected substantially constant pressure, and the injection is continued into the core sample at the selected pressure for a time period in the range of from about 1 hr. to about 30 days to insure that steady state flow conditions are reached. The temperature of the gas as it flows through the core sample is measured as is the very low flow rate of gas exiting the core sample. After steady state flow conditions are reached, the gas permeability of the core sample based on the gas injection pressure and the steady state gas temperature and flow rate is calculated.

Methods of determining the gas permeability reducing effect of injecting one or more treatment fluids into a subterranean formation having a very low permeability are also provided. Such methods basically comprise determining the initial gas permeability of a core sample of the subterranean formation as described above. After the initial gas permeability is determined, commonly referred to by those skilled in the art as the "native state permeability", a treatment fluid is injected into the core sample by way of the second end thereof until the core sample is saturated with the treatment fluid. Thereafter, the steps of injecting a gas into the core sample by way of the first end thereof at a selected substantially constant pressure and continuing such injection for a long period of time in the range of from about 1 hr. to about 30 days to obtain a steady state flow condition while measuring the temperature and flow rate of the gas exiting the core sample are repeated. The gas permeability of the core sample is then again calculated based on the gas injection pressure, the flow rate and the temperature of the gas, and the gas permeabilities of the core sample before and after injecting the treatment fluid are compared to determine if the injection of the treatment fluid caused permeability damage to the core sample whereby the permeability was reduced.

Apparatus for carrying out the methods of the present invention are also provided which basically comprise the above mentioned core sample container for confining a core sample and applying peripheral pressure thereon to simulate formation stress, means connected to the container for injecting a gas at a selected pressure into the container and through the core sample, means for measuring the temperature of the gas injected into and through the core sample and means for measuring the flow rate of gas injected into and through the core sample capable of continuously measuring flow rates in the range of from about $1 \times 10^{-7}$ to about 0.1 cubic centimeters per second.

It is, therefore, a general object of the present invention to provide methods and apparatus for determining the gas permeabilities of very low permeability subterranean gas formations and for determining the permeability reducing effects of injecting treatment fluids into such formations.

Other and further objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIG. 2 is a side cross-sectional view of the core sample test container utilized in the apparatus of FIG. 1.

DESCRIPTION OF PREFERRED EMBODIMENTS

Figure 1:
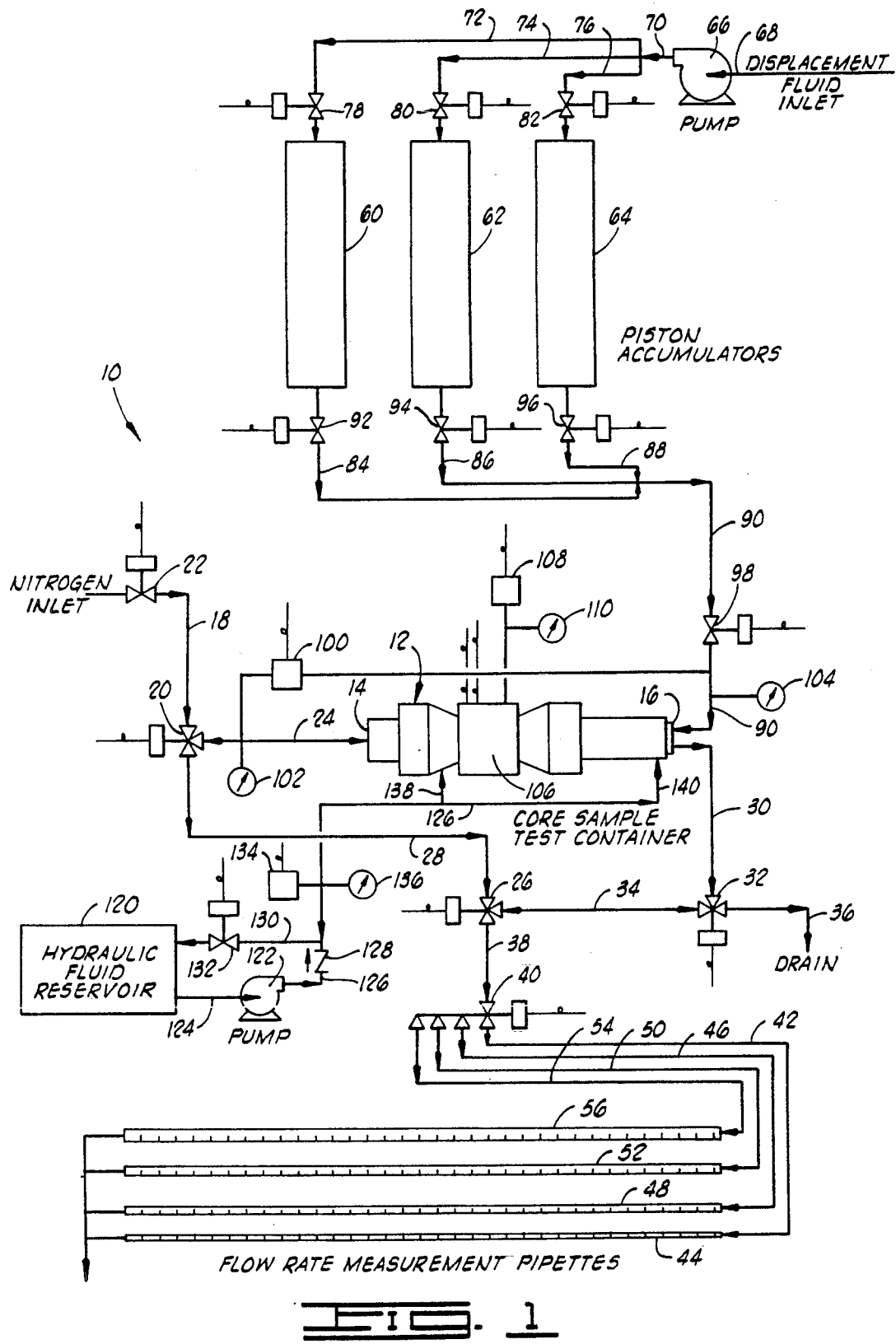
FIG. 1 is a schematic illustration of one form of test apparatus of the present invention.

Subterranean formations formed of very low permeability porous rock often contain substantial reserves of hydrocarbon gas. Typically, such formations have permeabilities of less than 1 milli-darcy and are associated with relatively low reservoir pressures, e.g., less than about 1000 psi, and low reservoir temperatures, e.g., about 100° F. Heretofore, it has been impossible to accurately determine the gas permeabilities of such formations with regard to the permeability damage effects of treatment fluids on the formations due primarily to the extremely low gas flow rates produced when core samples of the formations are tested.

The production of hydrocarbon gas from very low permeability subterranean formations can often be increased by stimulation procedures such as creating fractures in the rock making up the formations. However, if the fracturing and/or other treatment fluids utilized to perform the stimulation procedures reduce the permeabilities of the treated formations increases in production will not be realized. Heretofore, instead of stimulating the production of hydrocarbons from such formations, stimulation procedures have often resulted in losses of production.

The present invention provides methods and apparatus for accurately and reliably determining the gas permeabilities of low permeability subterranean formations, i.e., subterranean formations having permeabilities in the range of from about $1 \times 10^3$ to about $1 \times 10^{-3}$ micro-darcies. This invention also provides methods of determining the gas permeability reducing effect of injecting one or more treatment fluids into a low permeability formation so that treatment fluids having little or no such effect can be selected prior to carrying out a stimulation procedure in the formation.

THE METHODS

The methods of the present invention for determining the gas permeability of a subterranean formation wherein the permeability is in the range of from about $1 \times 10^3$ to about $1 \times 10^{-3}$ micro-darcies comprising the steps of:

(a) confining a core sample of the low permeability formation within a test container;

(b) applying pressure on the periphery of the core sample to simulate the confining stress in the formation and to seal the sides of the core sample whereby fluid injected into one end of the core sample is forced to flow through the core sample and out the other end thereof;

(c) injecting a gas into the core sample by way of said first end thereof at a selected substantially constant pressure in the range of from about 10 psig to about 1000 psig;

(d) continuing the injection of the gas into the core sample at the selected constant pressure for a time period in the range of from about 1 hr. to about 30 days to thereby insure a steady state flow condition is reached while measuring the temperature of the gas as it flows through the core sample and the flow rate of the gas exiting the core sample by way of the second end thereof; and (e) calculating the gas permeability of the core sample based on the gas injection pressure of step (c) and the flow rate and temperature measured in step (d).

The step of calculating the gas permeability of the core sample as described in step (e) above is performed using the following relationship:

$$K = \frac{(2 \times 10^6)BQ\mu L}{[(P + B)^2 - B^2]A}$$

wherein
K represents the permeability of the core sample in micro-darcies;
B represents the barometric pressure in atmospheres;
Q represents the gas flow rate at the barometric pressure in cubic centimeters per second;
$\mu$ represents the gas viscosity at the measured temperature of the gas in centipoises;
L represents the length of the core sample in centimeters;
A represents the cross-sectional area of the core sample in square centimeters; and
P represents the selected constant gas injection gauge pressure in atmospheres.

While various gases including methane can be utilized for conducting the methods of this invention, inert gases such as argon and nitrogen are generally preferred with nitrogen being the most preferred.

Examples of the magnitude of the various factors in the above relationship when nitrogen is utilized to test a very low permeability core sample are as follows:
Q = $1.0 \times 10^{-5}$ cc/sec
P = 100 psig which converts to 6.8046 atm
B = 27.65 inches of Hg which converts to 0.9281 atm
$\mu$ = 0.018325 cps (nitrogen)
L = 2.54 cm
A = 5.0671 cm$^2$ Substituting the above values in the above equation results in the calculation set forth as follows:

$$K = \frac{(2 \times 10^6)(0.9281 \text{ atm})(1.0 \times 10^5 \text{ cc/sec})(0.018325 \text{ cps})(2.54 \text{ cm})}{[(6.8046 \text{ atm} + 0.9281 \text{ atm})^2 - (0.9281 \text{ atm})^2](5.0671 \text{ cm}^2)}$$

K = $2.893 \times 10^{-3}$ micro-darcies.

Once the initial nitrogen gas permeability (native state permeability) of the core sample is determined as above, the core sample can be saturated with a treatment fluid and the effect of the treatment fluid on the formation can be determined. That is, the following additional steps can be carried out.

(f) Injecting or imbibing the treatment fluid into the core sample by way of the second end thereof at a selected substantially constant pressure in the range of from about 0 psig to about 2000 psig until the core sample is saturated with the treatment fluid or a desired injection time has elapsed or a desired volume has been imbibed. When the treatment fluid is injected and/or imbibed into the core sample, the injection or imbibition rate and the injected and/or imbibed treatment fluid volume can be measured by noting the rate and volume of gas and treatment fluid displaced from the core sample.

(g) Repeating steps (c), (d) and (e). That is, once the core sample has been invaded with the treatment fluid, a gas is again injected into the core sample by way of the first end thereof at the substantially constant pressure utilized in determining the native state permeability, and the injection is continued for a long time period in the range of from about 1 hr. to about 30 days until a steady state flow condition is reached. The temperature of the gas and the flow rate thereof are measured, and the gas permeability of the core sample is again calculated as described above. The gas permeabilities of the core sample before and after the treatment fluid was injected into the core sample are then compared to determine if the core sample was appreciably damaged by the treatment fluid.

The selected constant pressure at which the gas is injected into the core sample used to determine the native state permeability is generally a pressure which simulates the flowing pressure of gas through the subterranean formation from which the core sample was taken. As mentioned above, such flowing pressures are generally low, e.g., 10 to about 1000 psig, most often about 100 psig as used in the above permeability calculation example. The same pressure is utilized in determining the permeability of the core sample after saturation with the treatment fluid. However, in order to duplicate actual subterranean formation conditions, it is preferred that the gas injection be initially started at a higher pressure, e.g., 500 psig to simulate reservoir displacement pressure. The high pressure is preferably held for an initial period of time, e.g., 1 to 2 hours, and then lowered to the same pressure used in determining the native state permeability, e.g., 100 psig.

In both the native state gas permeability determination and the gas permeability determination after treatment fluid saturation, the gas injection is continued for long periods of time at the selected constant injection pressure, e.g., a time in the range of from about 1 hr. to about 30 days, to insure that steady state flow rate and equilibrium conditions have been reached in the core sample. After treatment fluid saturation, the gas injection brings about at least a partial removal of the treatment fluid from the core sample and the long term gas injection is required for steady state flow conditions to again be reached.

The comparison of the gas permeabilities of the core sample before and after saturation with a treatment fluid shows the reduction in the permeability caused by the treatment fluid. The gas permeability of the core sample following treatment fluid saturation and after having gas flow therethrough for a significantly long period of time demonstrates the ability of the treatment fluid to be recovered from the core sample and the rate at which such recovery can be achieved as well as the reduction in permeability caused by the treatment fluid.

Treatment fluids which are commonly used in stimulating subterranean formations include liquids, gelled liquids, foams and emulsions. In carrying out fracturing techniques in very low permeability subterranean formations, aqueous fracturing fluids are commonly utilized.

THE APPARATUS

Referring now to the drawings and particularly to FIG. 1, a presently preferred apparatus of this invention for carrying out the methods described above is schematically illustrated and generally designated by the numeral 10.

The apparatus 10 includes a core sample test container 12 which is preferably of the Hassler sleeve type and includes an internal bladder to which hydraulic fluid pressure is applied to exert peripheral pressure on a core sample confined therewithin. As mentioned above, both radial and axial pressure are applied on the core sample which simulates formation stress and seals the sides of the core sample whereby fluid injected into one end of the core sample is forced to flow through the core sample to the other end. The container 12 has a first end 14 which is provided with an inlet for injecting a gas into one end of the core sample. The other end 16 of the container 12 includes an outlet through which gas exiting the core sample flows and an inlet through which one or more treatment fluids can be injected into the core sample in a direction opposite to that of the gas injection.

A conduit 18 connected to a source of pressurized gas such as methane, argon, nitrogen or other inert gas, preferably nitrogen, leads pressurized gas to a three-way valve 20. A two-way shut off valve 22 is disposed in the conduit 18 between the three-way valve 20 and the source of the gas. While the valves 20 and 22 and the other valves to be described hereinbelow can be hand operated, they are preferably motor operated as shown in FIG. 1 whereby a computer operated control system can be utilized to automatically open and close them in accordance with a predetermined sequence. One of the outlet ports of the three-way valve 20 is connected to the pressurized gas inlet in the end 14 of the container 12 by a conduit 24. The other outlet port of the three-way valve 20 is connected to an inlet port of a three-way valve 26 by a conduit 28.

The gas outlet in the end 16 of the container 12 is connected by a conduit 30 to an inlet port of a three-way valve 32. A port of the three-way valve 32 is connected to a port of the three-way valve 26 by a conduit 34 and another port of the valve 32 is connected by a conduit 36 to a drain or other waste disposal location. The remaining port of the three-way valve 26 is connected by a conduit 38 to the inlet port of a four-way valve 40. The four outlet ports of the valve 40 are each connected to traveling oil meniscus flow meters, i.e., volume graduated pipettes containing oil meniscuses. Each of the four pipettes may be of different sizes so that a range of very low flow rate continuous measurements can be made. The traveling meniscus flow meters are capable of continuously measuring low flow rates in the range of from about $1 \times 10^{-7}$ to about 0.1 cubic centimeters per second over long periods of time, e.g., up to about 30 days.

More specifically, a first outlet port of the three-way valve 40 is connected by a conduit 42 to a flow rate measurement pipette 44 which is, for example, of a 0–0.1 cc size. A second outlet port of the valve 40 is connected by a conduit 46 to another pipette 48 which may be of the same or a different size than the pipette 44, e.g., a 0–0.5 cc size. The next port of the valve 40 is connected by a conduit 50 to a pipette 52 which may be of yet a larger size, e.g., a 0–1.0 cc size. The last port of the valve 40 is connected by a conduit 44 to another larger pipette, e.g., a 0–2.0 cc size. During testing, the valve 40 can be switched to an appropriate size pipette to measure the gas flow rate produced. The pipettes measure flow rate by the travel of the oil meniscus contained within the pipettes down the length thereof as a function of time. The number of pipettes and the size arrangement of the pipettes is not critical to the function of the apparatus 10.

One or more treatment fluids to be tested are contained within three piston displacement accumulators 60, 62 and 64. Prior to use, the accumulators are filled with the fluid or fluids to be tested, and O-ring sealed pistons are placed above the fluid levels in the tops of the accumulators. Displacement fluid, e.g., oil or water is pumped into the accumulators above the pistons by a special continuous syringe pump 66 which is capable of accurately pumping extremely low flow rates of fluid at either constant pressure or constant flow rate. A particularly suitable such pump capable of operating at pressures up to about 3,750 psi and producing constant flow rates from about 0.1 micro-liter per minute to about 170 milli-liters per minute is a model 500D syringe pump marketed by ISCO, Inc. of Lincoln, Neb.

The inlet connection of the pump 66 is connected by a conduit 68 to a source of displacement fluid and the outlet is connected by a conduit 70 to three conduits 72, 74 and 76 having shut-off valves 78, 80 and 82 disposed therein, respectively. The conduits 72, 74 and 76 are connected to inlet connections in the tops of the piston accumulators 60, 62 and 64, respectively. The outlet connections at the bottoms of the piston accumulators 60, 62 and 64 are connected by conduits 84, 86 and 88, respectively, to a conduit 90 which is in turn connected to the treatment fluid inlet in the end 16 of the core sample test container 12. The conduits 84, 86 and 88 have shut-off valves 92, 94 and 96 disposed therein, respectively, and the conduit 90 includes a shut-off valve 98 disposed therein. The various gas and treatment fluid conduits are preferably formed of a low dead-volume tubing such as 1/16 inch diameter chromatographic tubing.

A differential pressure transducer 100 is operably connected between the conduits 24 and 90, and calibrated high resolution pressure gauges 102 and 104 are connected to the conduits 24 and 90, respectively.

An electrically powered and controlled heater 106 may be connected to the core sample test container 12 for controlling the temperature of the core sample and the gas flowing therethrough during testing. A temperature transducer 108 and temperature indicator 110 are operably connected to the heater 106.

A hydraulic fluid reservoir 120 is provided, and the suction of a pump 122 is connected to the reservoir 120 by a conduit 124. The discharge of the pump 122 is connected by a conduit 126 to a pair of conduits 138 and 140 which are in turn connected to hydraulic fluid inlet connections in the core sample test container 12. As will be described further hereinbelow, the hydraulic fluid pressure exerted by the pump 122 is transmitted to the core sample confined within the test container 12. A check valve 128 is disposed in the conduit 126 adjacent the pump 122, and a hydraulic fluid return conduit 130 is connected between the conduit 126 and the hydraulic fluid reservoir 120 downstream of the check valve 128. A shut-off valve 132 is disposed in the conduit 130. A hydraulic fluid pressure transducer 134 and a pressure indicator 136 are also attached to the conduit 126 downstream of the check valve 128.

As will be understood, the pressure transducers 100 and 134 and the temperature transducer 108 are operably connected to one or more recording devices in the control system of the apparatus 10 whereby the pressures and temperatures sensed by the transducers can be continuously recorded during operation of the apparatus 10.

THE CORE SAMPLE TEST CONTAINER 12

Referring now to FIG. 2, the core sample test container 12 is illustrated in detail. While various types of core sample test containers can be used in the apparatus 10, a Hassler sleeve of the type and design illustrated in FIG. 2 is presently preferred. Such a Hassler sleeve including temperature control cell, control system and other accessories is commercially available from the Phoenix Instruments Company of Humble, Tex.

The core sample test container 12 (Hassler sleeve) is comprised of a core holder body 150 having a stationary ram 152 sealingly held within the body 150 by a quick change collar 154 (the outer end of the stationary ram 152 forms the end 14 of the container 12 previously described). The conduit 24 for conducting pressurized gas to the container 12 is connected to a passage 156 disposed in the stationary ram 152. Sealingly clamped to the interior of the stationary ram 152 by a clamp member 158 is a tubular resilient bladder member 160. The bladder member 160 is disposed within the body 150 and is clamped to a piston-ram member 162 by a clamp 164 at its other end. The internal end of the piston-ram 162 has a ram tip 166 sealingly connected thereto. A low permeability core sample 168 is disposed within the bladder member 160 between the internal end of the stationary ram 152 and the internal end of the ram tip 166 connected to the piston-ram 162. The piston-ram 162 is slidably and sealingly disposed within a piston housing 168 which is in turn connected to the body 150 at the opposite end thereof from the quick change collar 154. The ram tip 166 includes a pair of passages 170 and 172 formed therein and the previously described conduits 30 and 90 are connected to the passage 170 and 172. An internal piston sleeve 174 is provided which is sealingly and slidably connected internally of the piston-ram 162 and which provides a passage through which the conduits 30 and 90 pass.

A port 180 is provided in the body 150 which communicates the exterior of the body 150 to an annular space between the interior of the body 150 and the exterior of the resilient bladder 160. The previously described hydraulic fluid conduit 138 is threadedly connected to the port 180 and to the previously described hydraulic fluid conduit 126. A port 182 is provided in the piston housing 268 which communicates the exterior of the piston housing 268 to the interior thereof at a point adjacent the exterior end of the piston-ram 162. The previously described hydraulic fluid conduit 140 is threadedly connected to the port 182 and to the conduit 126.

The heating apparatus 106 is attached to the core holder body 150 and includes a thermal couple 140 to which the previously described temperature transducer 108 and temperature indicator 110 are connected. Electric power is supplied to the heater 106 by way of a cord 142 connected thereto.

THE OPERATION OF THE CORE SAMPLE CONTAINER 12

In operation of the core sample test container 12, the quick change collar 152 is removed from the body 150, and the resilient bladder 160 is removed from the stationary ram 152 by means of the removable clamp 158 whereupon the core sample 168 is inserted within the bladder 160. The bladder 160 is reconnected to the stationary ram 152 and the stationary ram 152 and quick change collar 154 are reinstalled in the body 150. Hydraulic pressure is next applied to the container 12 by way of the conduits 126, 138 and 140, which causes radial pressure to be applied to the sides of the core sample 168 by the bladder 160. That is, the bladder 160 is moved into pressurized contact with the core sample 168 by the entry of pressurized hydraulic fluid through the port 180 into the annular space between the exterior of the bladder 160 and the interior of the body 150. Simultaneously, pressurized, hydraulic fluid enters the interior of the piston housing 268 by way of the conduit 140 and port 182 causing the piston-ram 162 and ram tip 166 to be moved into forcible contact with the core sample 168 and force it against the interior end of the stationary ram 152 whereby axial pressure is applied to the core sample 168 corresponding to the radial pressure applied thereto. As indicated above, the particular pressure level applied to the core sample is selected to simulate the stress within the subterranean formation from which the core sample was taken.

The heater 106 is controlled so that the core sample 168 and the gas flowing therethrough by way of the passages 156 and 172 are maintained at a selected constant temperature during the operation of the test apparatus 10. The temperature is selected to simulate the gas temperature within the subterranean formation from which the core sample 168 was taken.

THE OPERATION OF THE APPARATUS 10

In operation of the apparatus 10, a core sample is confined within the core sample test container 12 as described above, and the hydraulic pump 122 is operated with the shut-off valve 132 closed to place the core sample under radial and axial pressure which simulates formation stress on the core sample. As mentioned, the heater 106 is operated to maintain the core sample at a temperature which simulates the temperature of the subterranean formation from which the core sample 168 was taken. Once the selected pressure is exerted on the core sample, the hydraulic fluid pump 122 is stopped.

The gas shut-off valve 122 is opened, the three-way valve 120 is positioned such that the gas flows from the conduit 18 into the conduit 24, the three-way valve 32 is positioned so that the gas exiting the core sample test container 12 flows by way of the conduit 34 to the three-way valve 26, the three-way valve 26 is positioned so that the conduit 34 is communicated with the conduit 38 and the four-way valve 40 is positioned so that the conduit 38 is communicated with one of the conduits 42, 46, 50 or 54 connected to a selected flow rate measurement pipette 44, 48, 52 or 56, respectively. The pressure of the gas flowing into the end 14 of the test container 12 by way of the conduit 24 is controlled at a selected constant pressure, and the very low flow rate of gas injected into and through the core sample 168 within the container 12 flows out of the container 12 by way of the conduit 30 connected thereto to one of the flow rate measurement pipettes wherein the flow rate is continuously indicated. As mentioned above, the injection of gas into the core sample 168 at the selected constant pressure is continued for a time period in the range of from about 1 hr. to about 30 days to insure steady state flow conditions are reached while the temperature of the gas and the flow rate of the gas exiting the core sample are measured. Once steady state flow conditions have been achieved, the native state permeability of the core sample is determined as described above.

The valve 22 is next closed, the three-way valve 20 is switched whereby the conduit 24 is communicated with the conduit 28, the valve 98 is opened, the three-way valve 26 is switched whereby the conduit 28 is communicated with the conduit 34 and the three-way valve 32 is switched whereby the conduit 34 is communicated with the conduit 36.

The valves around one of the piston accumulators 60, 62 or 64 containing the treatment fluid to be tested are opened, e.g., the valves 82 and 96 in the conduits 76 and 88 connected to the piston accumulator 64 are opened. The pump 66 is started whereby displacement fluid forces the piston within the piston accumulator 64 downwardly, and treatment fluid is caused to flow by way of the conduit 88 and the conduit 90 into and through the core sample 168 within the test container 12. During this phase, accurate monitoring of the treatment fluid injection and/or imbibition rate and volume can be conducted by measuring the oil meniscus movement in one of the traveling oil meniscus flow meters and the total fluid displaced downstream of the core sample 168. The total fluid volume determined by this method accurately reflects the volume of fluid which entered the core sample 168. That is, both the volume and rate of imbibed treatment fluid into the core sample before pressurized injection took place and the volume and rate of injected treatment fluid are measured. The term "introducing" is used hereinafter with respect to treatment fluids invading the core sample to mean and include either or both of injecting the treatment fluid into the core sample or allowing the treatment fluid to be imbibed into the core sample. Excess treatment fluid which exits the test container 12 can be removed by way of the conduit 24 and the conduits 28, 34 and 36 which conduct the fluid to a drain or other point of disposal. Once the core sample 168 has become completely saturated, or a desired treatment fluid volume has entered the core sample, or treatment fluid injection has taken place for a desired time period, the pump 66 is stopped. The valve 98 is then closed and the valves 20, 22, 26 and 32 are switched whereby gas is again flowed through the core sample 168 and the temperature and flow rate of gas exiting the core sample are continuously measured. The injection of the gas through the core sample 168 is again continued for a long period of time in the range of from about 1 hr. to about 30 days to insure steady state flow conditions are again reached while continuously measuring the temperature and flow rate of the gas exiting the core sample. Once a steady state flow condition has been obtained, the gas permeability of the core sample is again determined as described above, and the gas permeabilities before and after the treatment fluid injection are compared to determine the effect of the treatment fluid on the core sample.

As will be understood by those skilled in the art, the various conduits, valves and other structure of the apparatus 10 are of a small size such that the very low flow rates of gas passing therethrough do not accumulate in dead spaces within the apparatus 10 and an improved resolution of flow rate is obtained. In addition, more than one treating fluid can be simultaneously injected into the core sample being tested and/or components of a treating fluid can be mixed from two or more of the accumulators 60, 62 and 64 prior to being injected into the core sample. Also, as mentioned above, the operation of the apparatus 10 can be by hand or, more preferably, automatically controlled by a computer and other conventional control apparatus, the operation of which is well known to those skilled in the art.

In order to further illustrate the methods and apparatus of the present invention the following example is given.

EXAMPLE

A test in accordance with the present invention was performed to analyze the effect of a treatment fluid on the permeability of the lower Huron member of a Devonian shale formation in West Virginia.

A core sample was obtained and prepared for the test as follows. A whole core was taken from the formation by using air mist as the coring fluid and an aluminum inner liner core barrel device known to those skilled in the art of coring. Core plugs were then obtained from the whole core by drilling core plugs using nitrogen as a coolant in order to preserve the core's natural state. Each core plug weighed around 25 grams, had a length of approximately 1 inch and had a diameter of approximately 1 inch. A test core sample was prepared by shaving the ends of one of the core plugs using a sharp blade to remove core-end damage and plugging debris. The core sample was carefully inspected prior to testing to insure the core sample did not contain visible microfractures. The core sample was wrapped with one layer of teflon tape and placed within the core sample test container 12 of the apparatus 10.

After the core sample was in place in the container 12, hydraulic fluid was pumped by the pump 122 into the container to load the core sample with radial and axial hydraulic pressure of approximately 1200 psig. This pressure served as an approximation of the average stress in the rock of the low permeability, low pressure reservoir from which the core sample was taken. The hydraulic fluid used was a water dyed with a fluorescent tracer to check for possible leaks using ultraviolet light.

Next, nitrogen gas was introduced into the container 12 by way of the valve 22, the conduit 18, the valve 20, the conduit 24 and the passage 156 in the stationary ram 152 of the container 12 under an upstream steady pressure of approximately 100 psig. The downstream flow rate of the nitrogen gas, the barometric pressure, the temperature of the core sample and the $N_2$ gas and the upstream gauge pressure were periodically measured as the $N_2$ gas flowed through the core sample. The permeability of the core sample to the nitrogen gas (hereinafter "the $N_2$ permeability of the core") was calculated based on the above described measurements until the $N_2$ permeability of the core sample achieved a steady state condition. The $N_2$ permeability of the core was presumed to achieve a steady state condition at some value of irreducible connate fluid saturation. The steady state $N_2$ permeability of the core sample represented the native state $N_2$ permeability of the core sample.

The downstream flow rate of the nitrogen gas was measured using one of the traveling oil meniscus flow rate measurement pipettes 44, 48, 52 or 56 connected to the end 16 of the container 12 by way of the valve 40, the conduit 38, the valve 26, the conduit 34, the valve 32 and the conduit 30. The barometric pressure was measured using a mercury barometer located in the test facility room. The upstream gauge pressure was measured using the calibrated high resolution pressure gauge 102 located upstream of the core sample. The $N_2$ permeability of the core sample was calculated using the downstream flow rate of the nitrogen gas, the barometric pressure, the gas viscosity (corrected based on the gas temperature, the upstream gauge pressure and the core sample dimensions in accordance with the relationship described above.

Once the native state $N_2$ permeability of the core sample was determined, the core sample was saturated with a treatment fluid comprised of an aqueous solution containing 2% by weight potassium chloride. The treatment fluid was pumped into the core sample through the end 16 of the test container 12 under a constant pressure of 500 psig by way of the pump 66, the conduits 68, 70, 76, 88 and 90, the valves 82, 96 and 98 and the piston accumulator 64. The treatment fluid was pumped into the core until it was determined that the core was fully saturated therewith. It was determined that the core was fully saturated with the treatment fluid when fluid breakthrough occurred followed by stable permeability response to fluid injection.

After the core was fully saturated with the treatment fluid, nitrogen gas flow through the core from the end 14 of the test container 12 was re-started. The nitrogen gas was initially introduced into the core at a constant upstream pressure of 500 psig to simulate reservoir displacement pressure. This pressure was held for approximately 60 to 120 minutes and then lowered to approximately 100 psig the pressure at which the native state $N_2$ permeability of the core was determined. The nitrogen gas was continuously introduced into the core at approximately 100 psig for a long period of time (i.e., 16 days) to insure that a steady state flow and equilibrium were obtained and to evaluate long term clean-up response of the test fluid on the gas permeability of the core sample. The downstream flow rate of the nitrogen gas, the barometric pressure, the temperature of the $N_2$ gas and the upstream $N_2$ gas pressure were measured, and the $N_2$ permeability of the core sample was calculated based thereon periodically through out the test period. The $N_2$ gas flow was discontinued and the test terminated when no change or improvement in permeability was observed.

A comparison of the $N_2$ permeability of the core sample after saturation of the core sample with the treatment fluid (calculated to be 9.54 micro-darcies) to the native state $N_2$ permeability of the core sample (calculated to be 333.53 micro-darcies) shows that a drastic reduction in the $N_2$ permeability of the core sample was caused by the treatment fluid.

The $N_2$ permeability of the core after saturation with a treatment fluid and after having nitrogen gas flow therethrough for a significant period of time demonstrates the ability of the treatment fluid to be recovered from the core sample and the rate at which such recovery can be achieved. In the case tested, the aqueous solution of 2% potassium chloride did not clean up well at all and permanent damage was done to the permeability of the core sample.

Thus, the present invention is well adapted to carry out the objects and attain the ends and advantages mentioned as well as those which are inherent therein. While numerous changes may be made by those skilled in the art, such changes are encompassed within the spirit of this invention as defined by the appended claims.

What is claimed is:

1. A method of determining the gas permeability of a subterranean formation wherein such permeability is in the range of from about $1 \times 10^3$ to about $1 \times 10^{-3}$ microdarcies comprising the steps of:
   (a) confining a core sample of said low permeability formation having first and second ends within a test container;
   (b) applying pressure on the periphery of said core sample to simulate the confining stress in said formation and to seal the sides of said core sample whereby fluid injected into one end thereof is forced to flow to the other end;
   (c) injecting a gas into said core sample by way of said first end thereof at a selected substantially constant pressure;
   (d) continuing the injection of said gas into said core sample at said selected constant pressure for a period of time in the range of from about 1 hr. to about 30 days to insure a steady state flow while measuring the temperature of said gas as it flows through said core sample and the flow rate of said gas exiting said core sample by way of said second end thereof; and
   (e) calculating the gas permeability of said core sample based on the gas injection pressure of step (c) and the flow rate and temperature measured in step (d) in accordance with the following relationship $$K = \frac{(2 \times 10^6) BQ\mu L}{[(P + B)^2 - B^2]A}$$

wherein
K represents the gas permeability in microdarcies;
B represents barometric pressure in atmospheres;
O represents the gas flow rate measured in step (d) in cubic centimeters per second;
$\mu$ represents the gas viscosity in centipoises at the temperature measured in step (d);
L represents the core sample length in centimeters;
A represents the core sample cross-sectional area in square centimeters; and
P represents the selected constant gas injection gauge pressure of step (c) in atmospheres.

2. The method of claim 1 wherein the flow rate of gas exiting said core sample by way of said second end thereof is measured in accordance with step (d) by flowing said gas into a traveling oil meniscus flow meter and noting the volume represented by the movement of said oil meniscus per unit time.

3. The method of claim 1 wherein said gas is nitrogen.

4. A method of determining the gas permeability reducing effect of injecting a treatment fluid into a subterranean formation having a low permeability in the range of from about $1 \times 10^3$ to about $1 \times 10^{-3}$ microdarcies comprising the steps of:
   (a) confining a core sample of said subterranean formation having first and second ends within a test container;
   (b) applying pressure on the periphery of said core sample to simulate the confining stress in said formation and to seal the sides of said core sample whereby fluid injected into one end thereof is forced to flow to the other end;
   (c) injecting a gas into said core sample by way of said first end thereof at a selected substantially constant pressure;
   (d) continuing the injection of said gas into said core sample at said selected constant pressure for a period of time in the range of from about 1 hr. to about 30 days to insure a steady state flow while measuring the temperature of said gas as it flows through said core sample and the flow rate of said gas exiting said core sample by way of said second end thereof;
   (e) calculating the gas permeability of said core sample based on the gas injection pressure of step (c) and the flow rate and temperature measured in step (d) in accordance with the following relationship:

$$K = \frac{(2 \times 10^6) BQ\mu L}{[(P + B)^2 - B^2]A}$$

wherein
K represents the gas permeability in micro-darcies;
B represents barometric pressure in atmospheres;
Q represents the gas flow rate determined in step (d) in cubic centimeters per second;
$\mu$ represents the gas viscosity in centipoises at the temperature determined in step (d);
L represents the core sample length in centimeters;
A represents the core sample cross-sectional area in square centimeters; and
P represents the selected constant gas injection gauge pressure of step (c);
   (f) introducing a treatment fluid into said core sample by way of said second end thereof;
   (g) repeating steps (c), (d) and (e); and
   (h) comparing the gas permeabilities of said core sample calculated in accordance with step (d) before and after introducing said treatment fluid into said core sample.

5. The method of claim 4 wherein the flow rate of gas exiting said core sample by way of said second end thereof is measured in accordance with step (d) by flowing said gas into a traveling oil meniscus flow meter and noting the volume represented by the movement of said oil meniscus per unit time.

6. The method of claim 4 wherein said gas is selected from the group consisting of methane, argon, nitrogen and other inert gases.

7. The method of claim 4 wherein said treatment fluid is a fluid selected from the group consisting of a liquid, a gelled liquid, an emulsion and a foam.

8. The method of claim 4 which further comprises the step of maintaining said core sample at a selected substantially constant temperature to simulate the temperature of said formation.

9. The method of claim 4 wherein said gas is injected into said core sample in accordance with step (c) at a pressure in the range of from about 10 to about 1000 psig.

10. The method of claim 4 wherein said treatment fluid is injected into said core sample at a selected substantially constant pressure in the range of from about 0 to about 2000 psig.

* * * * *